(12) United States Patent
Mandava et al.

(10) Patent No.: US 11,408,954 B2
(45) Date of Patent: Aug. 9, 2022

(54) SYSTEMS AND METHODS OF REDUCING NOISE AND ARTIFACTS IN MAGNETIC RESONANCE IMAGING

(71) Applicant: GE Precision Healthcare LLC, Milwaukee, WI (US)

(72) Inventors: Sagar Mandava, Chandler, AZ (US); Ty A. Cashen, Madison, WI (US); Daniel Litwiller, Denver, CO (US); Ersin Bayram, Houston, TX (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 176 days.

(21) Appl. No.: 16/828,610

(22) Filed: Mar. 24, 2020

(65) Prior Publication Data

US 2021/0302525 A1    Sep. 30, 2021

(51) Int. Cl.
*G06K 9/00*      (2022.01)
*G01R 33/56*     (2006.01)
*G06T 7/00*      (2017.01)
*G06N 3/08*      (2006.01)
*A61B 5/055*     (2006.01)

(52) U.S. Cl.
CPC .......... *G01R 33/5608* (2013.01); *A61B 5/055* (2013.01); *G06N 3/088* (2013.01); *G06T 7/0012* (2013.01); *G06T 2207/10088* (2013.01); *G06T 2207/20081* (2013.01); *G06T 2207/20084* (2013.01)

(58) Field of Classification Search
CPC ............ G01R 33/5608; G01R 33/4824; G01R 33/5601; A61B 5/055; G06N 3/088; G06T 7/0012; G06T 2207/10088; G06T 2207/20081; G06T 2207/20084

USPC ......................................................... 382/128
See application file for complete search history.

(56) References Cited

U.S. PATENT DOCUMENTS

| 10,635,943 B1* | 4/2020 | Lebel ................... G06K 9/6262 |
| 2019/0104940 A1* | 4/2019 | Zhou ..................... G06T 11/005 |

(Continued)

OTHER PUBLICATIONS

Andreas Hauptmann et al., "Real-time cardiovascular MR with spatio-temporal artifact suppression using deep learning-proof of concept in congenital heart disease," Magnetic Resonance in Medicine, 2019, p. 1143-1156.

(Continued)

*Primary Examiner* — Van D Huynh
(74) *Attorney, Agent, or Firm* — Armstrong Teasdale LLP

(57) ABSTRACT

A computer-implemented method of reducing noise and artifacts in medical images is provided. The method includes receiving a series of medical images along a first dimension, wherein the signals in the medical images having a higher correlation in the first dimension than the noise and the artifacts in the medical images. The method further includes, for each of a plurality of pixels in the medical images, deriving a series of data points along the first dimension based on the series of medical images, inputting the series of data points into a neural network model, and outputting the component of signals in the series of data points. The neural network model is configured to separate a component of signals from a component of noise and artifacts in the series of data points. The method further includes generating a series of corrected medical images based on the outputted component of signals.

20 Claims, 8 Drawing Sheets

(56) References Cited

U.S. PATENT DOCUMENTS

| | | | | |
|---|---|---|---|---|
| 2019/0377047 A1* | 12/2019 | Chen | .................. | G01R 33/5608 |
| 2020/0058106 A1* | 2/2020 | Lazarus | ............... | G06K 9/6273 |
| 2020/0249300 A1* | 8/2020 | Sandino | ............ | G01R 33/5608 |
| 2020/0305806 A1* | 10/2020 | Tang | .................... | A61B 6/5205 |
| 2021/0012543 A1* | 1/2021 | Hein | .................... | G06T 11/008 |
| 2021/0123999 A1* | 4/2021 | An | ....................... | G01R 33/481 |
| 2021/0145393 A1* | 5/2021 | Gao | .................... | A61B 6/5258 |
| 2021/0295474 A1* | 9/2021 | Wang | ................... | G06N 3/084 |
| 2022/0028133 A1* | 1/2022 | Ewald | ................. | G06N 3/0445 |

OTHER PUBLICATIONS

Yoseob Han et al., "Deep learning with domain adaptation for accelerated projection-reconstruction MR," Magnetic Resonance in Medicine, 2018, p. 1189-1205.

Andreas Kofler et al., "Spatio-Temporal Deep Learning-Based Undersampling Artefact Reduction for 2D Radial Cine MRI with Limited Training Data," IEEE Transactions on Medical Imaging, vol. 39, No. 3, 2020.

Salman Ui Hassan Dar et al., "A Transfer-Learning Approach for Accelerated MRI Using Deep Neural Networks," Magnetic Resonance in Medicine, 2020:00, 1-23.

* cited by examiner

SYSTEMS AND METHODS OF REDUCING NOISE AND ARTIFACTS IN MAGNETIC RESONANCE IMAGING

BACKGROUND

The field of the disclosure relates generally to systems and methods of reducing noise and artifacts, and more particularly, to systems and methods of reducing noise and artifacts in medical images using a neural network model.

Radial magnetic resonance imaging (MRI), where k-space raw data is acquired by a radial trajectory, is attractive in medical imaging due to its motion robustness and its ability to support accelerated imaging. While acquisition noise is present in all MRI, radial MRI is additionally plagued by artifacts in the form of streak artifacts. Artifacts may be caused by system imperfections such as gradient non-linearities, poor fat suppression, motion, or under-sampled data acquisition in accelerated imaging. In time resolved imaging such as contrast enhanced imaging, artifacts are exacerbated due to an increased level of under-sampling for increasing spatial and temporal resolutions.

BRIEF DESCRIPTION

In one aspect, a computer-implemented method of reducing noise and artifacts in medical images is provided. The method includes receiving a series of medical images of a volume of a subject along a first dimension, wherein the medical images include signals, noise, and artifacts, the signals having a higher correlation in the first dimension than the noise and the artifacts. The method further includes, for each of a plurality of pixels in the medical images, deriving a series of data points along the first dimension based on the series of medical images, inputting the series of data points into a neural network model, and outputting the component of signals in the series of data points. The neural network model is configured to separate a component of signals in the series of data points from a component of noise and artifacts in the series of data points. The method further includes generating a series of corrected medical images based on the outputted component of signals in the series of data points for each of the plurality of pixels.

In another aspect, a noise and artifact reduction system is provided. The noise and artifact reduction system includes a noise and artifact reduction computing device. The noise and artifact reduction computing device includes at least one processor electrically coupled to at least one memory device. The at least one processor is programmed to receive a series of medical images of a volume of a subject along a first dimension, wherein the medical images include signals, noise, and artifacts, the signals having a higher correlation in the first dimension than the noise and the artifacts. The at least one processor is further programmed to, for each of a plurality of pixels in the medical images, derive a series of data points along the first dimension based on the series of medical images, input the series of data points into a neural network model, and output the component of signals in the series of data points. The neural network model is configured to separate a component of signals in the series of data points from a component of noise and artifacts in the series of data points. The at least one processor is further programmed to generate a series of corrected medical images based on the outputted component of signals in the series of data points for each of the plurality of pixels.

DRAWINGS

DETAILED DESCRIPTION

Figure 1:
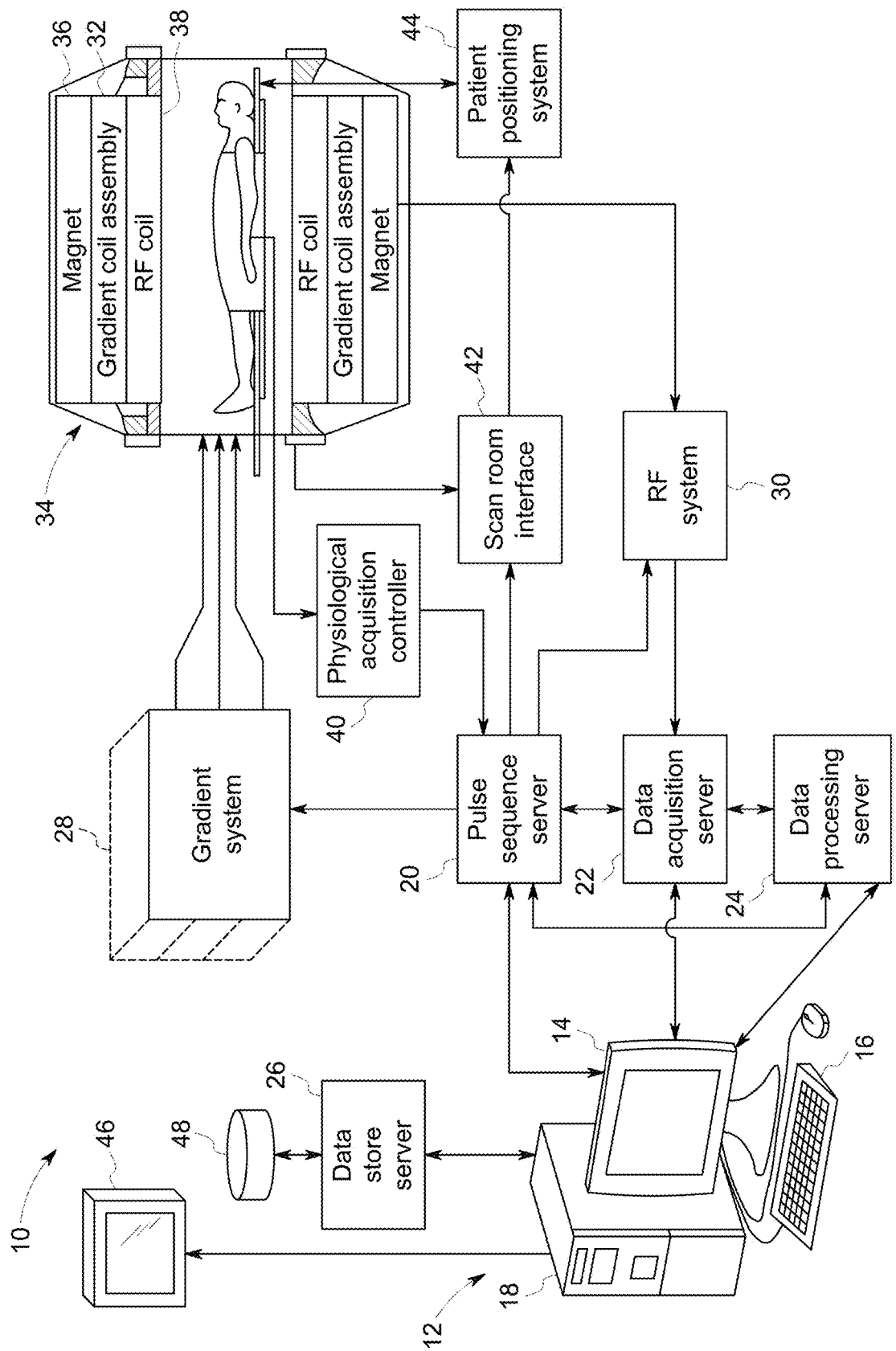
FIG. 1 is a schematic diagram of an exemplary magnetic resonance imaging (MRI) system.

The disclosure includes systems and methods of reducing noise and artifacts in medical images. In the systems and methods described herein, signals in medical images have a higher correlation than noise and artifacts in the medical images along the temporal dimension. Unlike signals, which represent the anatomies of the subject, artifacts are visual anomalies in the medical images that are not present in the subject, which may be caused by the imaging modality such as the pulse sequences, gradient non-linearities, poor fat saturation, or motion. A subject used herein is a human (live or deceased), an animal (live or deceased), or part of a human or an animal. Method aspects will be in part apparent and in part explicitly discussed in the following description.

While sparse or low rank reconstruction methods are available for minimizing artifacts, their uses are limited because of high computational complexity. The systems and methods described herein use a temporal neural network to suppress artifacts in a time series of images. Unlike most other neural networks, the neural network used herein is trained in an unsupervised manner. The time series of images are themselves used to train the neural network, which learns to separate the features or components in time series data. The result of this process is a network that reduces noise and artifacts in the images. The trained neural network takes the time series data as an input and provides a time series of data points with reduced noise and artifacts as an output.

For the purpose of detailed description, the imaging modality of MR systems, MR images such as MR images acquired by radial acquisition trajectories, and a series of MR images along the temporal dimension are used herein as examples only. The systems and methods described herein, however, are not limited to MR systems, MR images or MR images acquired by radial acquisition trajectories, or the temporal dimension. The system and methods described herein may be applied to other imaging modalities, such as computed tomography (CT) and positron emission tomography (PET), to a series of data points along other dimensions such as the spatial dimension or across multiple coils, and to a series of images acquired with other MR acquisition trajectories.

In magnetic resonance imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MRI image, a magnetic field (referred to as an excitation field B1), which is in the x-y plane and near the Larmor frequency, is generated by a radio-frequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses (Gx, Gy, and Gz) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

FIG. 1 illustrates a schematic diagram of an exemplary MRI system 10. In the exemplary embodiment, the MRI system 10 includes a workstation 12 having a display 14 and a keyboard 16. The workstation 12 includes a processor 18, such as a commercially available programmable machine running a commercially available operating system. The workstation 12 provides an operator interface that allows scan prescriptions to be entered into the MRI system 10. The workstation 12 is coupled to a pulse sequence server 20, a data acquisition server 22, a data processing server 24, and a data store server 26. The workstation 12 and each server 20, 22, 24, and 26 communicate with each other.

In the exemplary embodiment, the pulse sequence server 20 responds to instructions downloaded from the workstation 12 to operate a gradient system 28 and a radiofrequency ("RF") system 30. The instructions are used to produce gradient and RF waveforms in MR pulse sequences. An RF coil 38 and a gradient coil assembly 32 are used to perform the prescribed MR pulse sequence. The RF coil 38 is shown as a whole body RF coil. The RF coil 38 may also be a local coil that may be placed in proximity to the anatomy to be imaged, or a coil array that includes a plurality of coils.

In the exemplary embodiment, gradient waveforms used to perform the prescribed scan are produced and applied to the gradient system 28, which excites gradient coils in the gradient coil assembly 32 to produce the magnetic field gradients $G_x$, $G_y$, and $G_z$ used for position-encoding MR signals. The gradient coil assembly 32 forms part of a magnet assembly 34 that also includes a polarizing magnet 36 and the RF coil 38.

In the exemplary embodiment, the RF system 30 includes an RF transmitter for producing RF pulses used in MR pulse sequences. The RF transmitter is responsive to the scan prescription and direction from the pulse sequence server 20 to produce RF pulses of a desired frequency, phase, and pulse amplitude waveform. The generated RF pulses may be applied to the RF coil 38 by the RF system 30. Responsive MR signals detected by the RF coil 38 are received by the RF system 30, amplified, demodulated, filtered, and digitized under direction of commands produced by the pulse sequence server 20. The RF coil 38 is described as a transmitter and receiver coil such that the RF coil 38 transmits RF pulses and detects MR signals. In one embodiment, the MRI system 10 may include a transmitter RF coil that transmits RF pulses and a separate receiver coil that detects MR signals. A transmission channel of the RF system 30 may be connected to a RF transmission coil and a receiver channel may be connected to a separate RF receiver coil. Often, the transmission channel is connected to the whole body RF coil 38 and each receiver section is connected to a separate local RF coil.

In the exemplary embodiment, the RF system 30 also includes one or more RF receiver channels. Each RF receiver channel includes an RF amplifier that amplifies the MR signal received by the RF coil 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M = \sqrt{I^2 + Q^2} \qquad (1);$$

and the phase of the received MR signal may also be determined as in Eq. (2) below:

$$\varphi = \tan^{-1}\left(\frac{Q}{I}\right). \qquad (2)$$

In some embodiments, the pulse sequence server 20 also optionally receives subject data from a physiological acquisition controller 40. The controller 40 receives physiological signals from sensors connected to the subject, such as electrocardiograph ("ECG") signals from electrodes, or respiratory signals from a respiratory monitoring device such as a bellows. The physiological signals are typically used by the pulse sequence server 20 to synchronize, or "gate," the performance of the scan with the subject's heart beat or respiration.

In the exemplary embodiment, the pulse sequence server 20 also connects to a scan room interface circuit 42 that receives signals from sensors associated with the condition of the subject and the magnet system. Through the scan room interface circuit 42, a patient positioning system 44 receives commands to move the subject to desired positions before and/or during the scan.

In the exemplary embodiment, the digitized MR signal samples produced by the RF system 30 are received by the data acquisition server 22. The data acquisition server 22 may operate in response to instructions downloaded from the workstation 12 to receive real-time MR data and provide buffer storage such that no data is lost by data overrun. In some scans, the data acquisition server 22 does little more than pass the acquired MR data to the data processing server 24. In scans that need information derived from acquired MR data to control further performance of the scan, however, the data acquisition server 22 is programmed to produce the needed information and convey it to the pulse sequence server 20. For example, during prescans, MR data is acquired and used to calibrate the pulse sequence performed by the pulse sequence server 20. Also, navigator signals may be acquired during a scan and used to adjust the operating parameters of the RF system 30 or the gradient system 28, or to control the view order in which k-space is sampled.

In the exemplary embodiment, the data processing server 24 receives MR data from the data acquisition server 22 and processes it in accordance with instructions downloaded from the workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the exemplary embodiment, images reconstructed by the data processing server 24 are conveyed back to and stored at the workstation 12. In some embodiments, real-time images are stored in a database memory cache (not shown in FIG. 1), from which they may be output to operator display 14 or a display 46 that is located near the magnet assembly 34 for use by attending physicians. Batch mode images or selected real time images may be stored in a host database on disc storage 48 or on a cloud. When such images have been reconstructed and transferred to storage, the data processing server 24 notifies the data store server 26. The workstation 12 may be used by an operator to archive the images, produce films, or send the images via a network to other facilities.

Figure 2:
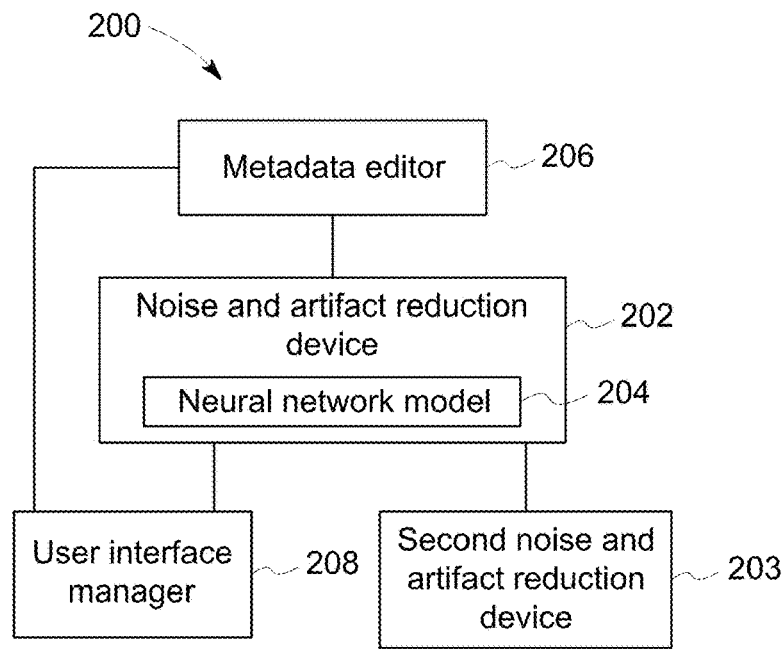
FIG. 2 is an exemplary noise and artifact reduction system.

FIG. 2 is a schematic diagram of an exemplary noise and artifact reduction system 200. In the exemplary embodiment, the system 200 includes a noise and artifact reduction computing device 202 configured to reduce noise and artifacts in medical images. The computing device 202 further includes a neural network model 204. The system 200 may include a second noise and artifact reduction computing device 203. The second noise and artifact reduction computing device 203 may be used to train neural network model 204, and the noise and artifact reduction computing device 202 may then use the trained neural network model 204. The second noise and artifact reduction computing device 203 may be the same computing device as the noise and artifact reduction computing device 202 such that the training and use of the neural network model 204 are on one computing device. Alternatively, the second noise and artifact reduction computing device 203 may be a computing device separate from the noise and artifact reduction computing device 202 such that the training and use of the neural network model 204 are executed on separate computing devices. The noise and artifact reduction computing device 202 may be included in the workstation 12 of the MRI system 10, or may be included on a separate computing device that is in communication with the workstation 12.

In the exemplary embodiment, the system 200 further includes a metadata editor 206 configured to update the metadata associated with the images. The system 200 may further include a user interface manager 208 configured to receive user inputs.

Figure 3:
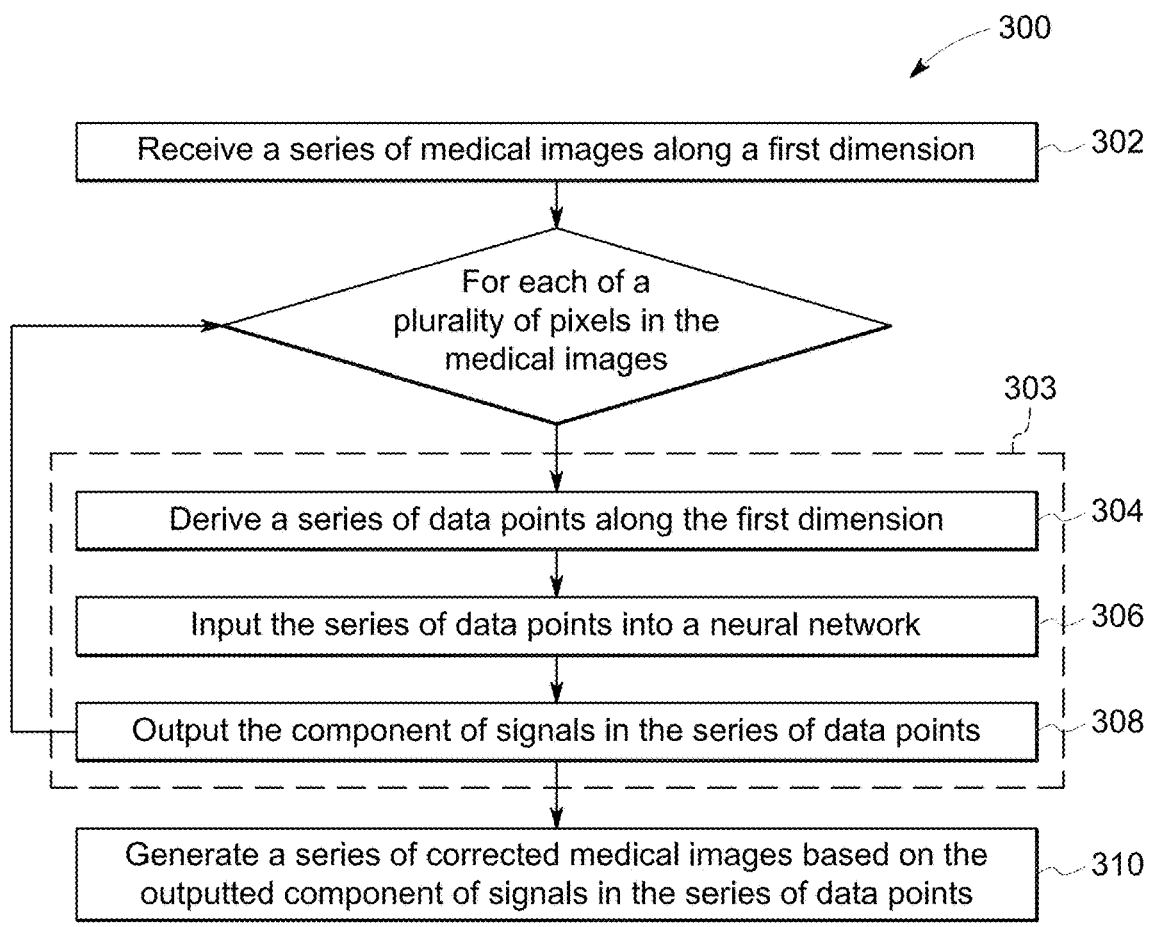
FIG. 3 is a flow chart of an exemplary method of reducing noise and artifacts.

FIG. 3 is a flow chart of an exemplary method 300 of reducing noise and artifacts in medical images. The method 300 may be executed in the noise and artifact reduction system 200. The method 300 includes receiving 302 a series of medical images of a volume in a subject along a first dimension. The series of medical images may be received from any suitable sources, such as the MRI system 10. The method 300 may further include receiving a series of raw data of the volume in the subject acquired by an imaging modality, wherein the series of raw data is along the first dimension, and reconstructing the series of raw data to derive the series of medical images. For example, a series of raw data is a series of k-space raw data of an abdomen of a subject acquired by a dynamic contrast enhancement (DCE) scan using an MRI system 10. A DCE scan typically images a volume in a subject multiple times while the subject is injected with a contrast agent. A DCE scan may be used to study a dynamic response of the subject, to achieve a different contrast of the anatomies from images acquired without a contrast agent, or both. The series of raw data include a series of sets of raw data along the time or temporal domain. That is, the series of raw data includes a series of sets of raw data acquired at different time points. In the series, each set of raw data may be in two dimension (2D), which is raw data of a slice, or may be in three dimension (3D), which is raw data of multi-slices or raw data acquired by a 3D acquisition.

In the exemplary embodiment, medical images include signals, noise, and artifacts. In the temporal dimension, signals have higher correlation than noise and artifacts. For each of a plurality of pixels in the medical images, the method 300 further includes reducing 303 noise and artifacts of the medical images. Reducing 303 noise and artifacts includes deriving 304 a series of data points along the first dimension based on the series of medical images, inputting 306 the series of data points into the neural network model 204, and outputting 308 the component of signals in the series of data points. The neural network model 204 is configured to separate a component of signals in the series of data points from a component of noise and artifacts in the series of data points. The plurality of pixels may be all or some of the pixels in the medical images. For example, if the series of medical images are medical images of resolution of 64×64×16 acquired at 12 different time points, the series of medical images would have 12 sets of medical images, each set having 3D medical images with a resolution of 64×64×16 in the x, y, and z dimensions and a total of 65,536 pixels. The first dimension is the temporal dimension, and the series of data points would have 12 data points. Reducing 303 noise and artifacts may be repeated for all 65,536 pixels, or may be repeated for a portion of the 65,536 pixels. Because the time series for a plurality of pixels are independent from each other, reducing 303 noise and artifacts for each pixel may be computed in parallel to increase the speed of the noise/artifact reduction process.

In the exemplary embodiment, the method 300 further includes generating 310 a series of corrected medical images based on the outputted component of signals in the series of data points for each of the plurality of pixels. Generating 310 a series of corrected medical images may be executed after completion of reducing 303 noise and artifacts for all of the plurality of pixels (as shown in FIG. 3), or may be executed inside the loop of reducing 303 noise and artifacts for each of the plurality of pixels. In generating 310 a series of correct medical images, for each of the plurality of pixels, the value of the medical images at that pixel is replaced with the component of signals. If reducing 303 noise and artifacts is not repeated for all pixels of the medical images, the corrected images may be derived by replacing values with outputted components of signals only at pixels performed with reducing 303 noise and artifacts. Because the neural network model 204 is configured to separate signals from noise and artifacts, the corrected medical images have less noise and artifacts than the originally-received images.

Figure 4A:
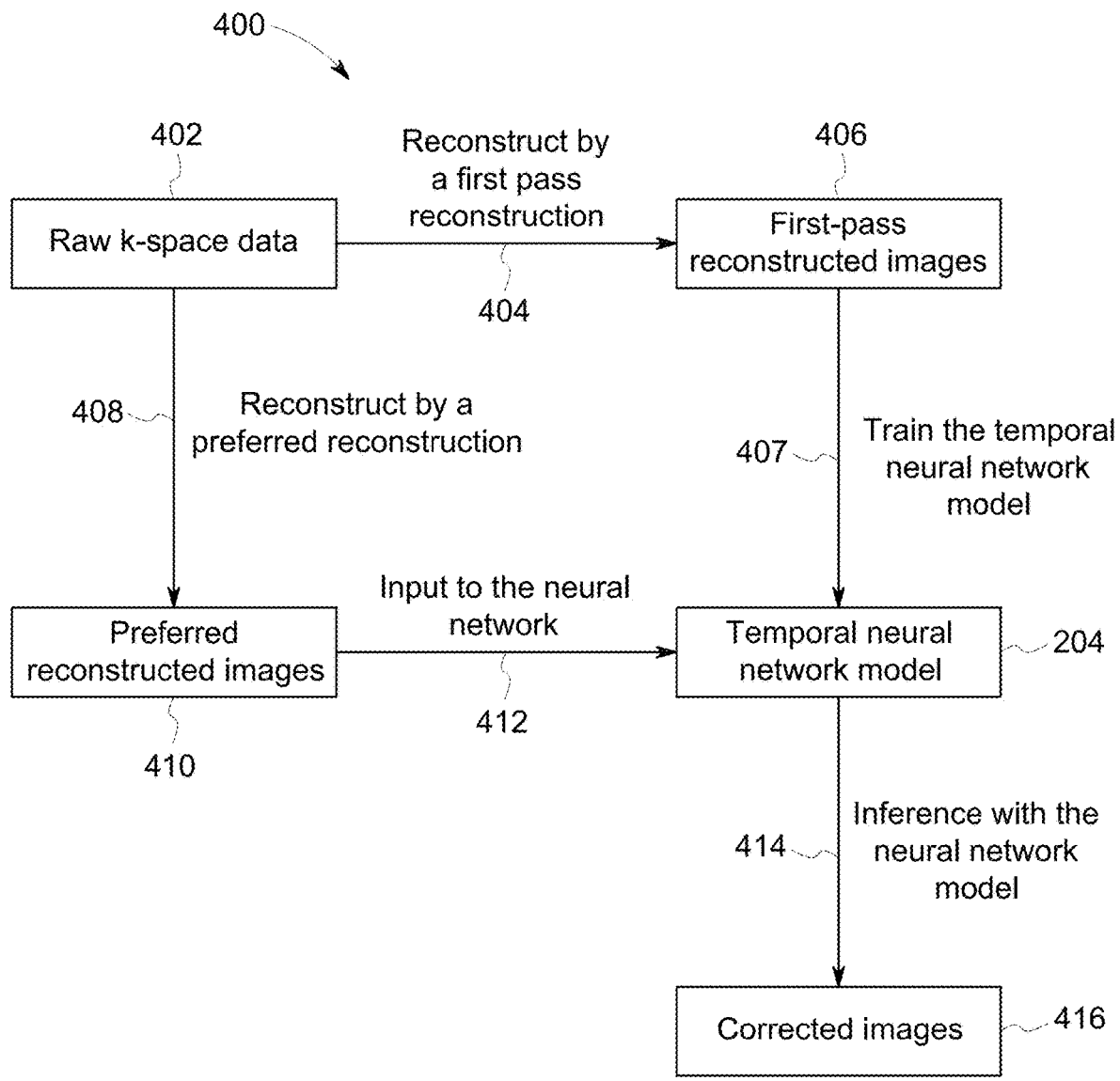
FIG. 4A is a schematic diagram of a data flow in an exemplary embodiment of the method shown in FIG. 3.
Figure 4B:
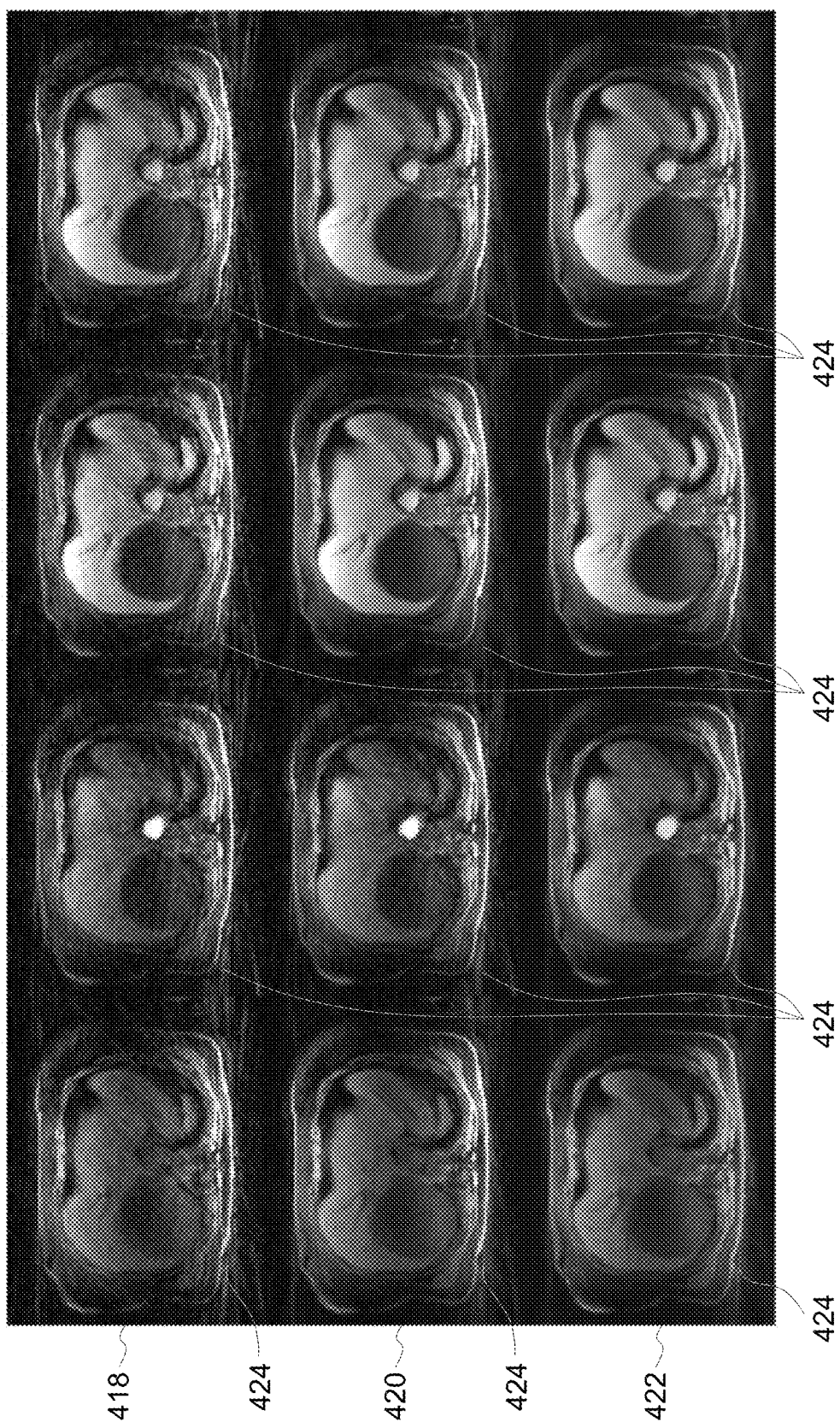
FIG. 4B shows magnetic resonance (MR) images processed with an exemplary method shown in FIG. 3 and with known methods.
Figure 4C:
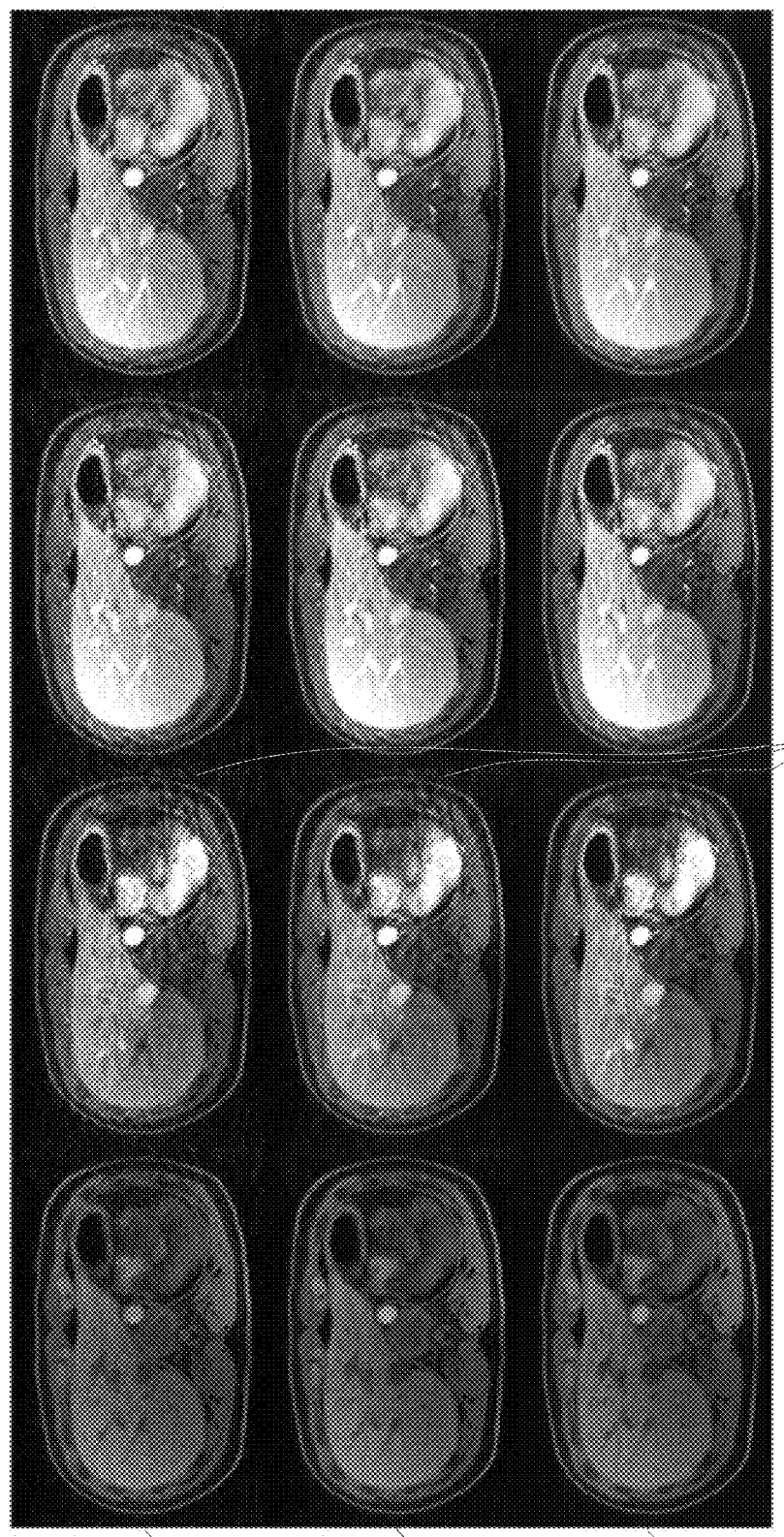
FIG. 4C shows MR images processed with another exemplary method shown in FIG. 3 and with known methods.

FIG. 4A shows a data flow 400 in an exemplary embodiment of the method 300. FIGS. 4B and 4C show comparison of images processed using the method 300 with images processed using known methods.

In the exemplary embodiment, a series of raw k-space data or raw data 402 are received. The series of raw data 402 may be acquired by time-resolved imaging, a DCE scan, diffusion weighted imaging, parameter mapping, function MRI, or with multiple number of acquisitions (NEX). The series of raw data 402 is reconstructed 404 by a first-pass reconstruction. A first-pass reconstruction may be a direct inversion of the raw data 402 into medical images such as using an inverse Fourier transform without any system correction or adjustments to the raw data 402 or reconstructed images such as routine adjustments performed by the system 10, for example a filtering of the raw data to reduce Gibbs ringing from step discontinuities. To further increase the computation speed, the reconstruction spatial resolution may be reduced in the first-pass reconstruction from the resolution of the acquired raw data 402. For example, if the imaging resolution of raw data 402 is 256×256, the raw data 402 may be reconstructed into images 406 having a resolution of 128×128 or less in the first-pass reconstruction. After the first-pass reconstruction, first-pass reconstructed images 406 of the raw data 402 are derived. The first-pass reconstructed images 406 are used to train 407 the neural network model 204. Because the neural network model 204 is trained by reconstructed images 406 of the same subject, the trained neural network model is patient specific. Advantageously, using first-pass reconstructed images 406 to train the neural network model 204 eliminates the need of large training datasets in typical supervised learning. All of the data needed for training the neural network model 204 is drawn from the acquired measurements themselves. Additionally, because the trained neural network model is patient specific, the trained neural network model is adapted to the specific patient and is a form of adaptive reconstruction/processing. As such, the neural network model may be robust to modeling mismatches, which may occur when offline training strategies are used.

In the exemplary embodiment, the raw data 402 may also be reconstructed 408 by a preferred reconstruction to derive preferred reconstructed images 410. The preferred reconstruction may be a reconstruction with adjustments performed by the system 10. With the adjustments, preferred reconstructed images 410 have better image quality than first-pass reconstructed images 406. The preferred reconstructed images 410 are inputted 412 to the trained neural network model 204, and are inferenced 414 by the neural network model 204 to derive corrected images 416. The corrected images 416 have reduced noise and artifacts. The corrected images 416 may be displayed on the operator display 14 or the display 46 of the MRI system 10.

In some embodiments, reconstructing 408 with a preferred reconstruction may not be performed. Instead, the raw data 402 is reconstructed 404 by the first-pass reconstruction, and the first-pass reconstructed images 406 are inputted into and inferenced by the trained neural network model 204. The neural network model 204 may be pre-trained. In one example, the neural network model 204 may be trained during the scanning once the raw data 402 has been received while waiting for the raw data 402 to be reconstructed 408 by a preferred reconstruction. In another example, the neural network model 204 may be trained during the scanning once part of the raw data 402 that are representative of the time series have been received while waiting for the rest of the scanning to be finished. Without system adjustments, first-pass reconstruction is faster than preferred reconstruction. Because the series of data points along the temporal dimension are independent for different pixels, training 407 and inferencing 414 may be performed in parallel for the different pixels. Further, because the series of data points along the temporal dimension has a much smaller number of data points than a typical image, the speed of training 407 and inferencing 414 by the neural network model 204 is much faster than a neural network model for image processing. In addition, the systems and methods described herein are compatible with any reconstruction and post-processing options because the preferred reconstruction is not limited to a certain reconstruction or post-processing option and the corrected images 416 may be inputted into any post-processing modules for further post-processing.

FIG. 4B shows four phases of a series of images acquired by a DCE scan with a radial imaging trajectory. The top row of images 418 are images without any filtering in the temporal dimension. A large amount of noise and artifacts 424 are present in images 418. The middle row of images 420 are images processed with a low rank filtering in the temporal dimension, which removes a linear component of noise and artifacts. The amount of noise and artifacts 424 in images 420 is less than the amount of noise and artifacts 424 in images 418. The bottom row of images 422 are images processed with the systems and methods disclosed herein. Noise and artifacts 424 in images 422 are significantly less than in images 418 or images 420. Images 418, 420, 422 are reconstructed with a preferred reconstruction, which includes system adjustments.

FIG. 4C shows images 468, 470, 472 acquired also by a DCE scan with a radial imaging trajectory but reconstructed by a direct inversion or a first-pass reconstruction, i.e., reconstructed by an inverse Fourier transform of the raw data. Similarly, the bottom row of images 472 are images processed with neural network filtering, while the middle row of images 470 are images processed with low rank filtering and the top row of images 468 are images without any temporal filtering. The amount of noise and artifacts 424 in images 472 is also much less than in images 468 or images 470, although the images are reconstructed by a first-pass reconstruction.

Figure 5A:
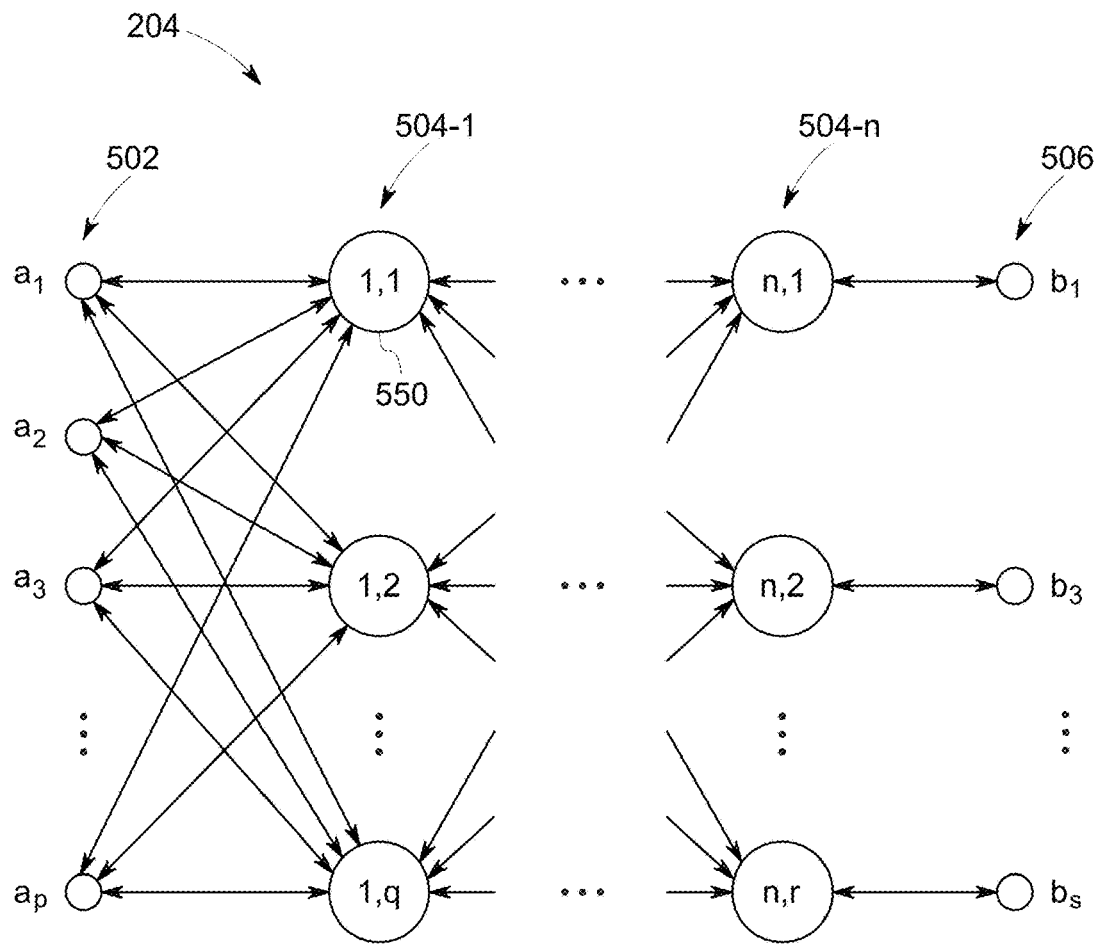
FIG. 5A is a schematic diagram of a neural network model.

FIG. 5A depicts an exemplary artificial neural network model 204. The exemplary neural network model 204 includes layers of neurons 502, 504-1 to 504-*n*, and 506, including an input layer 502, one or more hidden layers 504-1 through 504-*n*, and an output layer 506. Each layer may include any number of neurons, i.e., q, r, and n in FIG. 5A may be any positive integers. It should be understood that neural networks of a different structure and configuration from that depicted in FIG. 5A may be used to achieve the methods and systems described herein.

In the exemplary embodiment, the input layer 502 may receive different input data. For example, the input layer 502 includes a first input $a_1$ representing training images, a second input $a_2$ representing patterns identified in the training images, a third input $a_3$ representing edges of the training images, and so on. The input layer 502 may include thousands or more inputs. In some embodiments, the number of elements used by the neural network model 204 changes during the training process, and some neurons are bypassed or ignored if, for example, during execution of the neural network, they are determined to be of less relevance.

In the exemplary embodiment, each neuron in hidden layer(s) 504-1 through 504-*n* processes one or more inputs from the input layer 502, and/or one or more outputs from neurons in one of the previous hidden layers, to generate a decision or output. The output layer 506 includes one or more outputs each indicating a label, confidence factor, weight describing the inputs, and/or an output image. In some embodiments, however, outputs of the neural network model 204 are obtained from a hidden layer 504-1 through 504-*n* in addition to, or in place of, output(s) from the output layer(s) 506.

In some embodiments, each layer has a discrete, recognizable function with respect to input data. For example, if n is equal to 3, a first layer analyzes the first dimension of the inputs, a second layer the second dimension, and the final layer the third dimension of the inputs. Dimensions may correspond to aspects considered strongly determinative, then those considered of intermediate importance, and finally those of less relevance.

In other embodiments, the layers are not clearly delineated in terms of the functionality they perform. For example, two or more of hidden layers 504-1 through 504-$n$ may share decisions relating to labeling, with no single layer making an independent decision as to labeling.

Figure 5B:
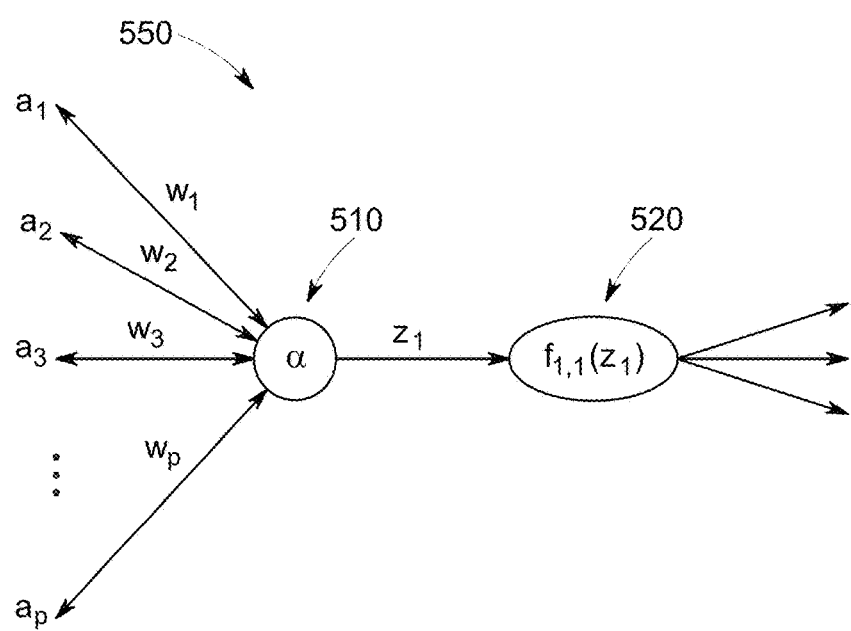
FIG. 5B is a schematic diagram of a neuron in the neural network model shown in FIG. 5A.

FIG. 5B depicts an example neuron 550 that corresponds to the neuron labeled as "1,1" in hidden layer 504-1 of FIG. 5A, according to one embodiment. Each of the inputs to the neuron 550 (e.g., the inputs in the input layer 502 in FIG. 5A) is weighted such that input $a_1$ through $a_p$ corresponds to weights $w_1$ through $w_p$ as determined during the training process of the neural network model 204.

In some embodiments, some inputs lack an explicit weight, or have a weight below a threshold. The weights are applied to a function $\alpha$ (labeled by a reference numeral 510), which may be a summation and may produce a value $z_1$ which is input to a function 520, labeled as $f_{1,1}(z_1)$. The function 520 is any suitable linear or non-linear function. As depicted in FIG. 5B, the function 520 produces multiple outputs, which may be provided to neuron(s) of a subsequent layer, or used as an output of the neural network model 204. For example, the outputs may correspond to index values of a list of labels, or may be calculated values used as inputs to subsequent functions.

It should be appreciated that the structure and function of the neural network model 204 and the neuron 550 depicted are for illustration purposes only, and that other suitable configurations exist. For example, the output of any given neuron may depend not only on values determined by past neurons, but also on future neurons.

The neural network model 204 may include a convolutional neural network (CNN), a deep learning neural network, a reinforced or reinforcement learning module or program, or a combined learning module or program that learns in two or more fields or areas of interest. Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. The neural network model 204 may be trained using unsupervised machine learning programs. In unsupervised machine learning, the processing element may be required to find its own structure in unlabeled example inputs. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, object statistics, and information. The machine learning programs may use deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing—either individually or in combination. The machine learning programs may also include natural language processing, semantic analysis, automatic reasoning, and/or machine learning.

Based upon these analyses, the neural network model 204 may learn how to identify characteristics and patterns that may then be applied to analyzing image data, model data, and/or other data. For example, the model 204 may learn to identify features in a series of data points.

Figure 6:
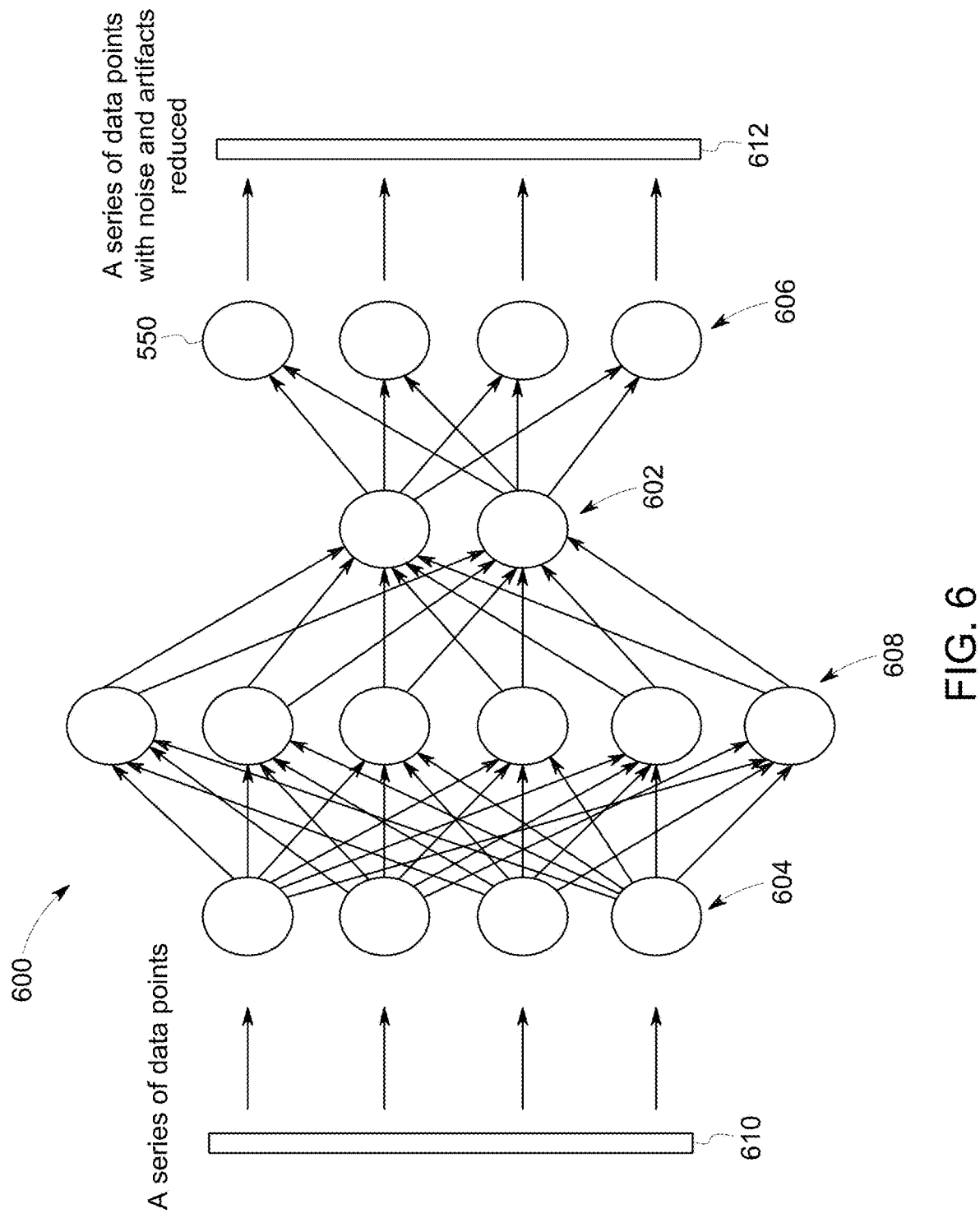
FIG. 6 is a schematic diagram of an exemplary neural network.

FIG. 6 shows an exemplary neural network 600 included in the neural network model 204. The neural network 600 is an autoencoder network. The neural network 600 includes a bottleneck layer 602 that has fewer neurons 550 than each of the input layer 604, the output layer 606, and other intermediate layer(s) 608. The bottleneck layer 602 forces the neural network 600 to learn the features of the input data. The neural network 600 is used here as an example for the purpose of illustration only. The neural network 600 may have different configurations, or be a different type of neural network.

In operation, a series of data points 610 along the temporal dimension is inputted into the input layer 604. Another series of data points 612 is outputted from the output layer 606. The series of data points 612 have the same number of data points as the series of data points 610, but with noise and artifacts reduced.

In the exemplary embodiment, the neural network 600 is an unsupervised neural network. An unsupervised neural network does not require a large amount of labelled training data, which may be challenging to acquire for medical images, especially for the same patient or for the same application. During training of the neural network 600, the neural network 600 takes one or more series of training data points as an input and outputs a series of data points. The neural network 600 is adjusted by reducing a loss function defined by a user to below a threshold level. Because signals in the series of data points have a higher correlation along the temporal dimension than noise and artifacts, the neural network 600 separates the component of signals from the component of noise and artifacts in the series of data points. In some embodiments, the neural network 600 is trained by an analytical model of the medical images. The analytical model may be a model of the series of medical images or the raw data acquired by the imaging modality. For example, MR signals and/or images may be simulated under predefined experimental conditions using simulators such as a Bloch simulator or using an Extended Phase Graph approach. MR signals and/or images may also be approximated using exponential models. The simulated MR signals and/or images are used to train the neural network 600, in placed of the raw k-space data 402 and/or the first-pass reconstructed images 406 (shown in FIG. 4A).

A series of data points 610 along the temporal dimension is used as an example for an illustration purpose only. The series of data points 610 may also be a series of data points across coils. For example, a series of raw data 402 of a volume of the subject are acquired by a plurality of coils. A series of medical images 406, 410 of the volume are reconstructed from the series of raw data 402. The 1D series of data points 610 for a specific pixel in the medical images 406, 410 are the data points at that specific pixel across the plurality of coils.

In another example, the medical images 406, 410 may be segmented into a plurality of segments, such as a foreground, a background, or specific organs like the liver. The reduction of noise and artifacts may be performed for the segments separately or for one or more segments only.

Figure 7:
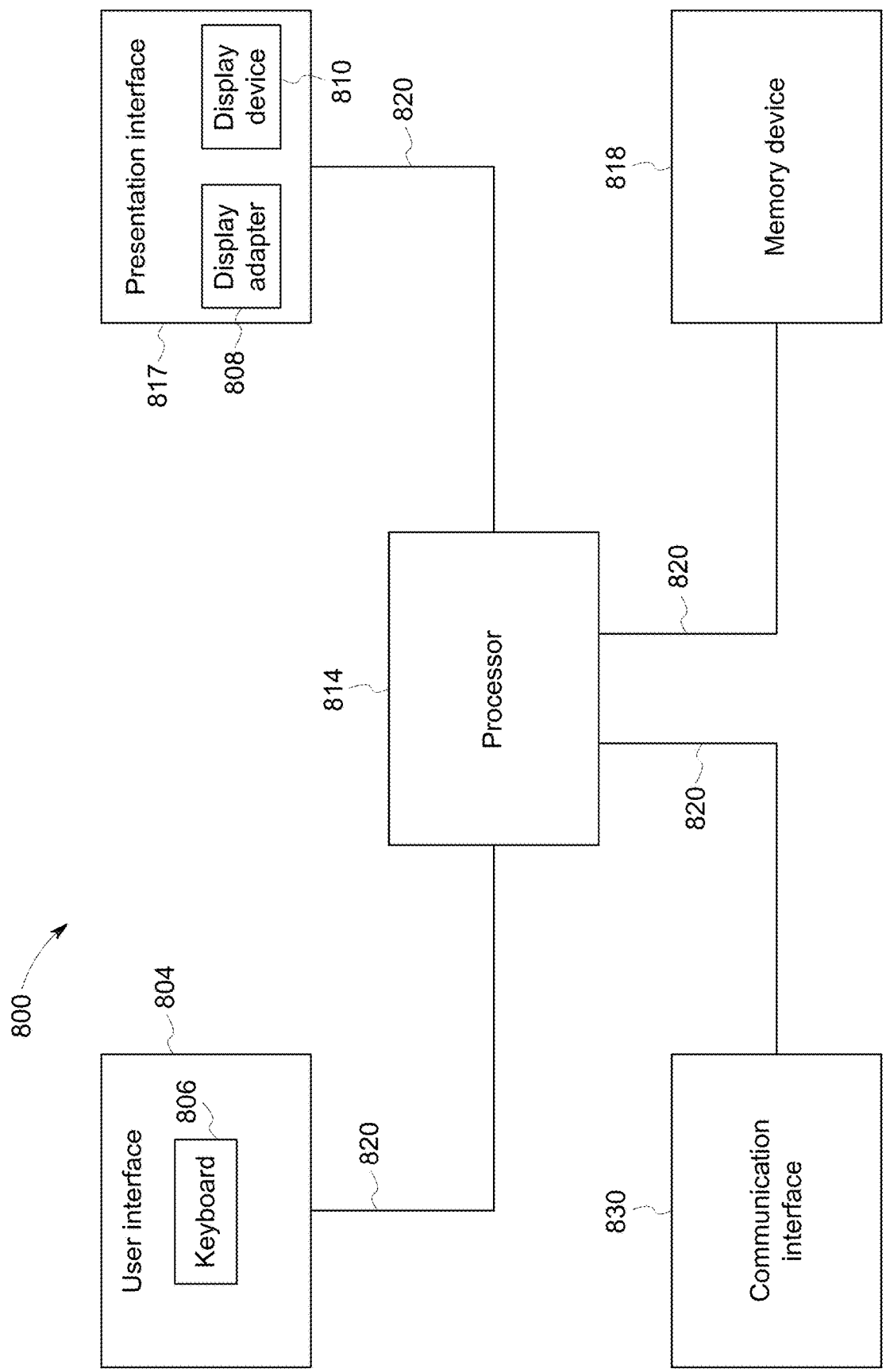
FIG. 7 is a block diagram of an exemplary computing device.

The workstation 12 and the noise and artifact reduction computing device 202, 203 described herein may be any suitable computing device 800 and software implemented therein. FIG. 7 is a block diagram of an exemplary computing device 800. In the exemplary embodiment, the computing device 800 includes a user interface 804 that receives at least one input from a user. The user interface 804 may include a keyboard 806 that enables the user to input pertinent information. The user interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a display interface 817 that presents information, such as input events and/or validation results, to the user. The display interface 817 may also include a display adapter 808 that is coupled to at least one display device 810. More specifically, in the exemplary embodiment, the display device 810 may be a visual display device, such as a cathode ray tube (CRT), a liquid crystal display (LCD), a light-emitting diode (LED) display, and/or an "electronic ink" display. Alternatively, the display interface 817 may include an audio output device (e.g., an audio adapter and/or a speaker) and/or a printer.

The computing device 800 also includes a processor 814 and a memory device 818. The processor 814 is coupled to the user interface 804, the display interface 817, and the memory device 818 via a system bus 820. In the exemplary embodiment, the processor 814 communicates with the user, such as by prompting the user via the display interface 817 and/or by receiving user inputs via the user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, the memory device 818 includes one or more devices that enable information, such as executable instructions and/or other data, to be stored and retrieved. Moreover, the memory device 818 includes one or more computer readable media, such as, without limitation, dynamic random access memory (DRAM), static random access memory (SRAM), a solid state disk, and/or a hard disk. In the exemplary embodiment, the memory device 818 stores, without limitation, application source code, application object code, configuration data, additional input events, application states, assertion statements, validation results, and/or any other type of data. The computing device 800, in the exemplary embodiment, may also include a communication interface 830 that is coupled to the processor 814 via the system bus 820. Moreover, the communication interface 830 is communicatively coupled to data acquisition devices.

In the exemplary embodiment, the processor 814 may be programmed by encoding an operation using one or more executable instructions and providing the executable instructions in the memory device 818. In the exemplary embodiment, the processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

At least one technical effect of the systems and methods described herein includes (a) reduction of noise and artifacts with reduced computation complexity; (b) patient-specific trained neural network; and (c) compatibility with any reconstruction and post-processing options.

Exemplary embodiments of systems and methods of reducing noise and artifacts are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method of reducing noise and artifacts in medical images, comprising:
   receiving a series of medical images of a volume of a subject along a first dimension, wherein the medical images include signals, noise, and artifacts, the signals having a higher correlation in the first dimension than the noise and the artifacts;
   for each of a plurality of pixels in the medical images,
     deriving a series of data points along the first dimension based on the series of medical images;
     inputting the series of data points into a neural network model, wherein the neural network model is configured to separate a component of signals in the series of data points from a component of noise and artifacts in the series of data points; and
     outputting the component of signals in the series of data points; and
   generating a series of corrected medical images based on the outputted component of signals in the series of data points for each of the plurality of pixels.

2. The method of claim 1, wherein the first dimension is a temporal dimension.

3. The method of claim 1, further comprising:
   receiving a series of raw data of the volume in the subject acquired by an imaging modality, wherein the series of raw data is along the first dimension; and
   reconstructing the series of raw data to derive the series of medical images.

4. The method of claim 3, wherein the series of raw data comprises a plurality of raw data of the volume acquired by a plurality of coils, and the first dimension is across the plurality of coils.

5. The method of claim 3, further comprising:
reconstructing the series of raw data using a first-pass reconstruction to derive a series of first-pass reconstructed images;
deriving a plurality of series of training data points based on the series of first-pass reconstructed images by, for each of a plurality of pixels in the first-pass reconstructed images, deriving a series of training data points along the first dimension based on the series of first-pass reconstructed images; and
training the neural network model using the plurality of series of training data points.

6. The method of claim 5, further comprising reconstructing the series of raw data with a preferred reconstruction to derive a series of preferred reconstructed images, wherein the series of preferred reconstructed images have higher image quality than the series of first-pass reconstructed images, wherein:
deriving a series of data points further comprises deriving the series of data points along the first dimension for each of the plurality of pixels based on the series of preferred reconstructed images; and
inputting the series of data points further comprises inputting the series of data points into the trained neural network model.

7. The method of claim 3, wherein:
reconstructing the series of raw data using a first-pass reconstruction to derive a series of first-pass reconstructed images;
deriving a series of data points further comprises deriving the series of data points along the first dimension for each of the plurality of pixels based on the series of first-pass reconstructed images; and
inputting the series of data points further comprises inputting the series of data points into a trained neural network model.

8. The method of claim 1, wherein the neural network model is an unsupervised neural network model.

9. The method of claim 8, wherein the neural network model is trained with a series of unlabeled training images.

10. The method of claim 8, further comprises training the neural network model with an analytical model representing the series of medical images.

11. A noise and artifact reduction system, comprising a noise and artifact reduction computing device, said noise and artifact reduction computing device comprising at least one processor electrically coupled to at least one memory device, and said at least one processor programmed to:
receive a series of medical images of a volume of a subject along a first dimension, wherein the medical images include signals, noise, and artifacts, the signals having a higher correlation in the first dimension than the noise and the artifacts;
for each of a plurality of pixels in the medical images,
derive a series of data points along the first dimension based on the series of medical images;
input the series of data points into a neural network model, wherein the neural network model is configured to separate a component of signals in the series of data points from a component of noise and artifacts in the series of data points; and
output the component of signals in the series of data points; and
generate a series of corrected medical images based on the outputted component of signals in the series of data points for each of the plurality of pixels.

12. The system of claim 11, wherein the first dimension is a temporal dimension.

13. The system of claim 11, said at least one processor further programmed to:
receive a series of raw data of the volume in the subject acquired by an imaging modality, wherein the series of raw data is along the first dimension; and
reconstruct the series of raw data to derive the series of medical images.

14. The system of claim 13, wherein the series of raw data comprises a plurality of raw data of the volume acquired by a plurality of coils, and the first dimension is across the plurality of coils.

15. The system of claim 13, said at least one processor further programmed to:
reconstruct the series of raw data using a first-pass reconstruction to derive a series of first-pass reconstructed images;
derive a plurality of series of training data points based on the series of first-pass reconstructed images by, for each of a plurality of pixels in the first-pass reconstructed images, deriving a series of training data points along the first dimension based on the series of first-pass reconstructed images; and
train the neural network model using the plurality of series of training data points.

16. The system of claim 15, said at least one processor further programmed to:
reconstruct the series of raw data with a preferred reconstruction to derive a series of preferred reconstructed images, wherein the series of preferred reconstructed images have higher image quality than the series of first-pass reconstructed images;
derive the series of data points along the first dimension for each of the plurality of pixels based on the series of preferred reconstructed images; and
input the series of data points into the trained neural network model.

17. The system of claim 13, said at least one processor further programmed to:
reconstruct the series of raw data using a first-pass reconstruction to derive a series of first-pass reconstructed images;
derive the series of data points along the first dimension for each of the plurality of pixels based on the series of first-pass reconstructed images; and
input the series of data points into a trained neural network model.

18. The system of claim 11, wherein the neural network model is an unsupervised neural network model.

19. The system of claim 18, wherein the neural network model is trained with a series of unlabeled training images.

20. The system of claim 18, said at least one processor further programmed to train the neural network model with an analytical model representing the series of medical images.

* * * * *